United States Patent

Yamaguchi

[11] Patent Number: 5,142,916
[45] Date of Patent: Sep. 1, 1992

[54] RUPTURE INITIATION INSPECTING METHOD AND APPARATUS

[75] Inventor: Takuro Yamaguchi, Kanagawa, Japan

[73] Assignee: Nissan Motor Company, Limited, Japan

[21] Appl. No.: 673,891

[22] Filed: Mar. 25, 1991

[30] Foreign Application Priority Data

Mar. 28, 1990 [JP] Japan .................. 2-80484

[51] Int. Cl.⁵ .......................................... G01M 19/00
[52] U.S. Cl. ........................................ 73/799; 73/162; 73/587
[58] Field of Search .................. 73/799, 162, 801, 587

[56] References Cited

U.S. PATENT DOCUMENTS

| | | | |
|---|---|---|---|
| 4,196,620 | 4/1980 | Dapiran | 73/162 |
| 4,380,172 | 4/1983 | Imam et al. | 73/587 X |
| 4,685,335 | 8/1987 | Sato et al. | 73/587 X |
| 4,931,949 | 6/1990 | Hernandez et al. | 73/162 X |

FOREIGN PATENT DOCUMENTS

| | | |
|---|---|---|
| 2008753 | 6/1979 | United Kingdom . |
| 2129560 | 5/1984 | United Kingdom . |
| 2228088 | 8/1990 | United Kingdom . |

*Primary Examiner*—Jerry W. Myracle
*Attorney, Agent, or Firm*—Lowe, Price, LeBlanc & Becker

[57] ABSTRACT

A method and apparatus for inspecting a rupture initiation in an article. While a load is applied to the article repetitively, an elastic wave is monitored by an elastic wave sensor which converts it into an electric signal. The electric signal is fed to a signal transmission device having a capacity of transmitting low-frequency components of the electric signal. The transmitted electric signal is divided into successive signal segments. The successive signal segments are averaged to produce an averaged signal waveform informing the presence of a rupture initiation in the article.

6 Claims, 3 Drawing Sheets

RUPTURE INITIATION INSPECTING METHOD AND APPARATUS

BACKGROUND OF THE INVENTION

This invention relates to a method and apparatus for inspecting a rupture initiation in articles of manufacture. Although the invention will be described in connection with a rupture test on a gear, it is to be understood that the invention is not limited in any way to such application and is equally applicable to inspect a rupture initiation in power transmission components used in automotive vehicles and other articles.

Endurance tests have been conducted on power transmission components used in automotive vehicles to ensure their strength against a predetermined number of repetitive applications of a constant load. For correct detection of an initiation of the rupture of a tested power transmission component, it is necessary to inspect a small rupture such as a crack in the power transmission component.

When a force is applied to a solid brittle article, elastic energy is stored at a point where stress concentration occurs in the article. When the concentrated stress exceeds a limit, the article is subject to plastic deformation and/or small rupture at the point, causing stress relaxation to release the stored elastic energy. A part of the released elastic energy is converted in the form of elastic wave (acoustic emission) propagating through the article. A well-known acoustic emission (AE) method utilizes the elastic wave to inspect a small rupture of the article. The acoustic emission method employs an elastic wave sensor attached to the article, a signal processor and a cable connected between the elastic wave sensor and the signal processor. However, the cable is twisted and eventually broken where the article is a rotary component tested while rotating.

In order to solve the problem, there is proposed, in Japanese Patent Kokai No. 63-271132, an elastic wave sensor attached to a bearing on which the rotary component is carried. Since the elastic wave sensor is separated from the rotary component to be tested, however, the elastic wave signal obtainable from the elastic wave sensor is attenuated to a great extent and it has noises superimposed thereon.

There is also proposed, in Japanese Patent Kokai No. 63-241350, an elastic wave sensor attached to an article to be tested. The elastic wave sensor includes an FM transmitter for transmitting a elastic wave signal at FM frequencies to the signal processing unit. However, the elastic wave sensor of this type is very expensive and sensitive to vibrations. The elastic wave sensor would be damaged if it is used for a fatigue test.

Slip rings are well known in the art as inexpensive signal transmission devices. However, such slip rings operate with sufficient efficiency for frequencies less than about 10 kHz. For this reason, they have not been used to transmit an elastic wave signal from an elastic wave sensor to a signal processing unit.

SUMMARY OF THE INVENTION

Therefore, it is a main object of the invention to provide an inexpensive method and apparatus which can inspect a rupture initiation in an article with high accuracy during a rupture test performed to repeat load application to the article.

In one aspect of the invention, there is provided a method of inspecting a rupture initiation in a gear. The method comprises the steps of setting the gear on a rotary shaft for rotation therewith at a position where the gear to be tested is in mesh engagement with a gear having a degree of resistance to rotation; rotating the rotary shaft; with an elastic wave sensor attached to the gear to be tested, sensing an elastic wave and converting the elastic wave into an electric signal; with a signal transmission device coupled to the elastic wave sensor, transmitting the electric signal, the signal transmission device having a capacity of transmitting low-frequency components of the electric signal; dividing the transmitted electric signal into a signal segment each time the rotary shaft rotates a full rotation; and averaging successive signal segments to produce an average signal waveform informing the presence of a rupture initiation in the gear to be tested.

In still another aspect of the invention, there is provided an apparatus for inspecting a rupture initiation in a gear. The apparatus comprises a rotary shaft on which a gear to be tested is fixed for rotation therewith; a gear held in mesh engagement with the gear to be tested, the gear having a degree of resistance to rotation; means for rotating the rotary shaft; an elastic wave sensor attached to the gear to be tested for sensing an elastic wave and converting the elastic wave into an electric signal; a signal transmission device coupled to the elastic wave sensor for transmitting the electric signal, the signal transmission device having a capacity of transmitting low-frequency components of the electric signal; and a signal processor coupled to the signal transmission device. The signal processor includes means for dividing the transmitted electric signal into a signal segment each time the rotary shaft rotates a full rotation, and means for averaging successive signal segments to produce an average signal waveform informing the presence of a rupture initiation of the gear to be tested.

BRIEF DESCRIPTION OF THE DRAWINGS

This invention will be described in greater detail by reference to the following description taken in connection with the accompanying drawings, in which.

DETAILED DESCRIPTION OF THE INVENTION

Figure 1:
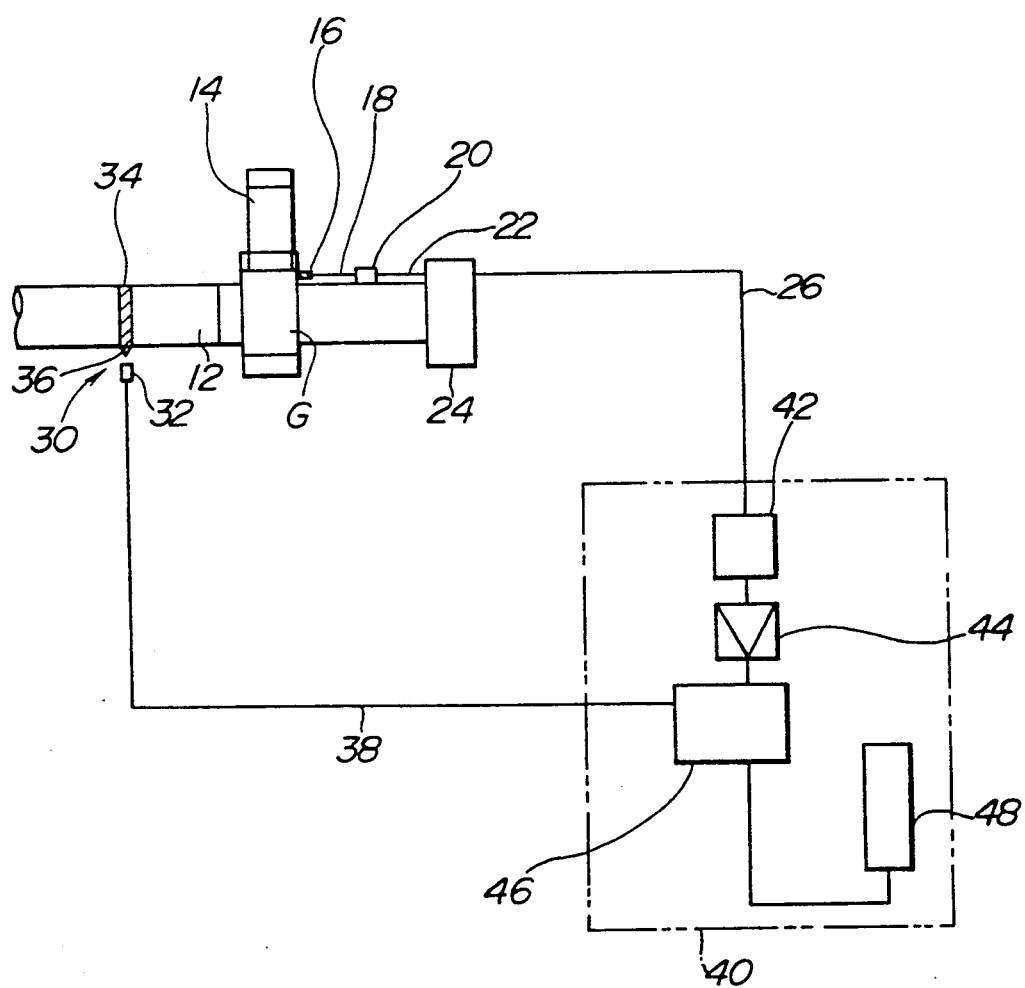
FIG. 1 is a schematic diagram showing a rupture initiation inspecting apparatus embodying the method and apparatus of the invention.
Figure 2:
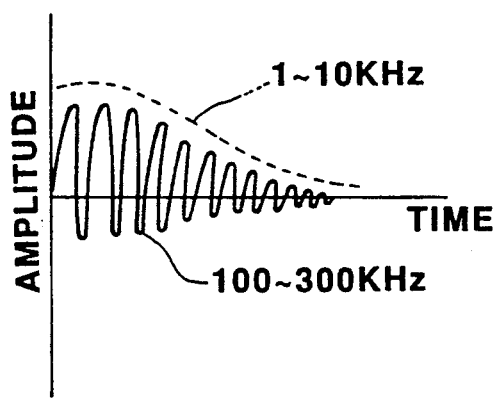
FIG. 2 contains a waveform obtained when a crack occurs in the gear to be tested.

With reference to the drawings, and in particular to FIG. 1, there is shown a schematic diagram of a rupture testing apparatus embodying the method and apparatus of the invention. In the illustrated case, the rupture testing apparatus is used to inspect a rupture initiation in a gear G. The rupture testing apparatus includes a rotary shaft 12 on which the gear G is mounted for rotation in unison therewith. A gear 14 is provided at a location adjacent to the rotary shaft 12 for mesh engagement with the gear G to provide a predetermined degree of resistance to rotation of the gear G. When the rotary shaft 12 is rotated by an electric motor or the like, the gear 14 repetitively applies a constant load (bending stress) to the root portion of each tooth of the gear G each time the rotary shaft 12 makes a full rotation. If a rupture is initiated in the gear G; that is, a crack appears in the root portion of one of the teeth of the gear G, an elastic wave will be produced each time the one tooth comes into engagement with the gear 14, as shown in FIG. 2. As can be seen from FIG. 2, the elastic wave contains high-frequency components having frequencies of 100 kHz to 300 kHz and low-frequency components having frequencies less than 10 kHz. Normally, the high-frequency components have been used to inspect the crack. Rather, according to the invention, the low-frequency components are used to inspect the crack. This permits the use of an inexpensive slip ring as a signal transmitting device.

Figure 3:
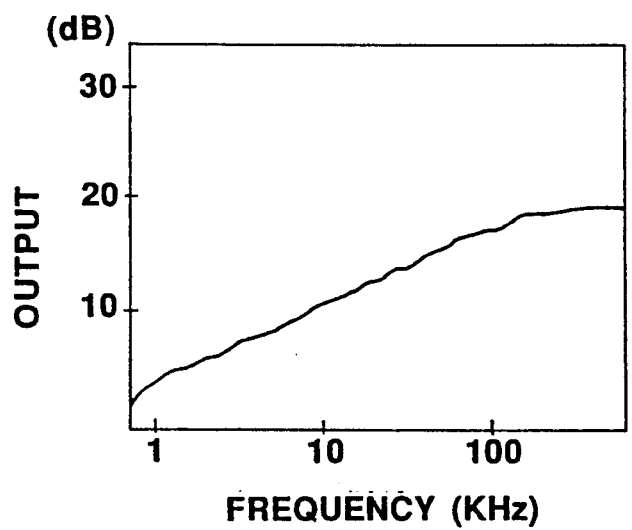
FIG. 3 is a graph showing the frequency characteristic of the slip ring used in the rupture initiation inspecting apparatus of FIG. 1.

The elastic wave is sensed by an elastic-wave or acoustic-emission sensor 16 attached to one side surface of the gear G. The elastic wave sensor 16 converts the sensed elastic wave into an electric elastic wave signal. FIG. 3 shows the frequency characteristic of the elastic wave sensor. The electric elastic wave signal is fed through a line 18 to a pre-amplifier 20 fixed on the rotary shaft 12 for rotation therewith. The pre-amplifier 20 has a predetermined amplification degree (in the illustrated case 26 dB) for amplifying the elastic wave signal to provide an improved signal-to-noise (S/N) ratio. The amplified elastic wave signal is then fed from the pre-amplifier 20 through a line 22 to a signal transmission medium taken in the form of a slip ring 24 mounted the rotary shaft 12 near its one end. The slip ring 24 operates with sufficient efficiency for frequencies less than about 10 kHz. Thus, the slip ring 24 has a capacity of transmitting the low-frequency components of the elastic wave signal.

The rotation of the rotary shaft 12 is sensed by a shaft rotation sensor, generally designated by the numeral 30. The shaft rotation sensor 30 may be taken in the form of a magnetic pickup transducer having an electric coil 32 which has an alternating voltage generated across its terminals as a result of changes in magnetic flux in its magnetic circuit. These flux changes are produced by a notch member 34 connected to the rotary shaft 12 for rotation therewith. The notch member 34 may have a single notch 36 so that the electric coil 32 produces a pulse each time the rotary shaft 12 makes a full rotation.

The rupture testing apparatus also includes a signal processing unit 40 which includes a band pass filter 42, a main amplifier 44, a data processor 46 and a waveform recording unit 48. The band pass filter 42 is connected through a line 26 to the slip ring 24. The band pass filter 42 filters out noise and passes signal components below 10 kHz to the main amplifier 44 which has a predetermined amplification degree (in the illustrated case 40 dB). The amplified signal is fed from the main amplifier 44 to the data processor 46 which also receives a pulse signal through a line 38 from the rotation sensor 30. The data processor 46 responds to pulses fed thereto from the shaft rotation sensor 30 by dividing the amplified signal fed thereto from the main amplifier 44 into signal waveform segments each fed from the main amplifier 44 between the successive pulses fed from the shaft rotation sensor 30; that is, for a full rotation of the rotary shaft 12. The divided signal waveform segments are successively stored in a memory included in the data processor 46. The data processor 46 averages a predetermined number of (in the illustrated case 256) stored signal waveform segments through a linear averaging technique to produce an averaged signal waveform. The linear averaging process is effective to enhance signal components which are produced in phase; that is, at the same angle of rotation of the rotary shaft 12 with respect to a reference position at which the notch 36 exists while at the same time attenuating occasional noise components to a great extent. The averaged signal waveform is outputted to the waveform recording unit 48.

The rupture testing apparatus of the invention was used to conduct an intermeshing endurance test on a cemented and hardened gear G made of case-hardening steel (SCr420H steel). The gear G was a 39-tooth spur gear (module 1.5) cemented and hardened to have an effective hardened layer depth of 0.7 mm and a surface hardness of HRC62. The rotary shaft 12 was rotated at a speed of 600 rpm under a torque of 100 kgm-m.

Figure 4:
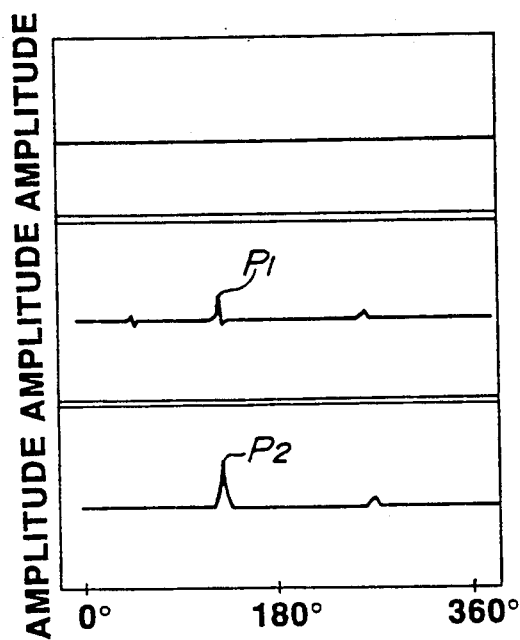
FIG. 4 contains three averaged signal waveforms obtained through linear averaging processes.

The test results are shown in the waveforms of FIG. 4. The ordinates of the waveforms represent the voltage magnitudes and the abscissae thereof represent the angles of rotation of the rotary shaft 12 with respect to the reference position. The upper waveform in the Figure shows an averaged signal waveform obtained for 256 successive signal waveform segments, the first signal waveform segment is stored when the number of rotation of the rotary shaft 12 is zero. It is to be noted that the linear averaging processes eliminates the background noises and provides a flat averaged signal waveform indicating no crack in the gear G. The average signal waveform obtained when no crack is produced in the gear G may be used as a reference waveform to eliminate noise components produced in phase. That is, it is possible to eliminate the noise components produced in phase from an average signal waveform by subtracting the reference waveform from the averaged signal waveform.

Figure 5:
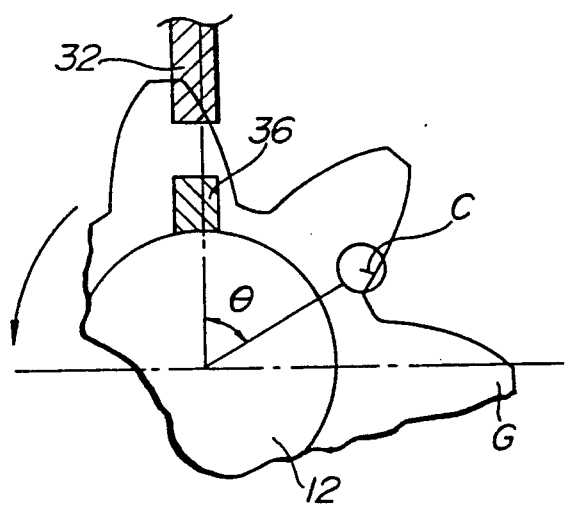
FIG. 5 is a schematic diagram showing the position of the crack in the gear with respect to the magnetic pickup sensor.

The second waveform of FIG. 4 shows an average signal waveform obtained for 256 successive signal waveform segments, the first signal waveform segment is stored when the number of rotations of the rotary shaft 12 is 10,000. It is to be noted that the average signal waveform includes a pulse P1 at an angle $\theta$ (about 140°) of rotation of the rotary shaft 12 with respect to the reference position at which the notch 36 exists. The pulse P1 indicates a crack produced in the gear G. The angle $\theta$ indicates the position of the crack with respect to the notch 36, as best shown in FIG. 5 where the character C indicates a crack produced in the root portion of a tooth of the gear G.

The third waveform of FIG. 4 shows an averaged signal waveform obtained for 256 successive signal waveform segments, the first signal waveform segment is stored when the number of rotations of the rotary shaft 12 is 20,000. The average signal waveform includes a pulse P2 at an angle $\theta$ (about 140°) of rotation of the rotary shaft 12 with respect to the reference position. It is to be noted that the pulses P1 and P2 appear in phase on the averaged signal waveforms FIG. 4. The pulse P2 is greater than the pulse P1. This indicates that the crack is increasing.

The endurance test was completed when the number of rotations of the rotary shaft 12 was 20,256. A crack was found at a position indicated by the pulses P1 and P2. The crack had a depth of 0.3 mm.

I claim:

1. A method of inspecting a rupture initiation in a gear, comprising the steps of:

setting the gear on a rotary shaft for rotation therewith at a position where the gear to be tested is in mesh engagement with a gear having a degree of resistance to rotation;

rotating the rotary shaft;

with an elastic wave sensor attached to the gear to be tested, sensing all elastic wave and converting the elastic wave into an electric signal;

with a signal transmission device coupled to the elastic wave sensor, transmitting the electric signal, the signal transmission device having a capacity of transmitting low-frequency components of the electric signal;

dividing the transmitted electric signal into a signal segment each time the rotary shaft rotates a full rotation; and averaging successive signal segments to produce an averaged signal waveform informing the presence of a rupture initiation in the gear to be tested.

2. The method as claimed in claim 1, wherein the signal transmission device is a slip ring mounted on the rotary shaft, the slip ring having a capacity of transmitting low-frequency components below 10 kHz.

3. The method as claimed in claim 1 wherein said dividing step further comprises the step of successively storing the signal segments in a storage device, and said averaging step comprises the further step of accessing the signal segments stored in the storage device and applying a linear averaging step thereto.

4. An apparatus for inspecting a rupture initiation in a gear, comprising:

a rotary shaft on which a gear to be tested is fixed for rotation therewith;

a gear held in mesh engagement with the gear to be tested, the gear having a degree of resistance to rotation;

means for rotating the rotary shaft;

an elastic wave sensor attached to the gear to be tested for sensing an elastic wave and converting the elastic wave into an electric signal;

a signal transmission device coupled to the elastic wave sensor for transmitting the electric signal, the signal transmission device having a capacity of transmitting low-frequency components of the electric signal; and a signal processor coupled to the signal transmission device, the signal processor including means for dividing the transmitted electric signal into a signal segment each time the rotary shaft rotates a full rotation, and means for averaging successive signal segments to produce an averaged signal waveform informing the presence of a rupture initiation of the gear to be tested.

5. The apparatus as claimed in claim 4, wherein the signal transmission device is a slip ring mounted on the rotary shaft, the slip ring having a capacity of transmitting low-frequency components below 10 kHz.

6. The apparatus as claimed in claim 4 wherein said signal processor includes storage means for storing a plurality of signal segments therein, said means for averaging being controlled to access the stored signal segments and to apply a linear averaging process thereto.

* * * * *